US009346058B2

(12) United States Patent
Yamamoto et al.

(10) Patent No.: US 9,346,058 B2
(45) Date of Patent: May 24, 2016

(54) UNIT FOR GRINDING SAMPLE, UNIT FOR GRINDING AND COLLECTING SAMPLE, AND PROCESS FOR GRINDING SAME

(75) Inventors: Takuji Yamamoto, Tokyo (JP); Kiyonori Higa, Tokyo (JP); Shunji Hattori, Tokyo (JP)

(73) Assignee: Nippi, Incorporated, Tokyo (JP)

( * ) Notice: Subject to any disclaimer, the term of this patent is extended or adjusted under 35 U.S.C. 154(b) by 367 days.

(21) Appl. No.: 13/480,877

(22) Filed: May 25, 2012

(65) Prior Publication Data

US 2012/0305685 A1    Dec. 6, 2012

(30) Foreign Application Priority Data

Jun. 1, 2011    (JP) .................................. 2011-123592

(51) Int. Cl.
*B02C 19/08* (2006.01)
*B02C 23/16* (2006.01)
*A61J 7/00* (2006.01)

(52) U.S. Cl.
CPC ............... *B02C 19/08* (2013.01); *A61J 7/0007* (2013.01); *B02C 23/16* (2013.01); *Y10S 241/27* (2013.01)

(58) Field of Classification Search
CPC ........ A61J 7/0007; Y10S 241/27; B02C 2/00; B02C 19/08; B02C 23/16
USPC ........... 241/24.1, 26, 27, 29, 68, 82, 82.1, 83, 241/274, 284, 30, 168, 169, 169.1, 169.2, 241/199, 199.1, 199.11, 301, DIG. 27
See application file for complete search history.

(56) References Cited

U.S. PATENT DOCUMENTS

| 4,366,930 | A  | * | 1/1983  | Trombetti, Jr. ................ 241/169 |
| 4,967,971 | A  | * | 11/1990 | Smith ............................ 241/169 |
| 5,829,696 | A  | * | 11/1998 | DeStefano et al. ........... 241/169 |
| 7,748,892 | B2 | * | 7/2010  | McCoy ...................... 366/176.3 |
| 2011/0308665 | A1 | * | 12/2011 | McKay ............................ 141/2 |

FOREIGN PATENT DOCUMENTS

| JP | 49-45986  | 12/1974 |
| JP | 50-19518  | 6/1975  |
| JP | 63-112974 | 5/1988  |

(Continued)

OTHER PUBLICATIONS

Japanese Office Action, Application No. 2012-121573 issued Nov. 26, 2013 (and translation).

*Primary Examiner* — Matthew G Katcoff
(74) *Attorney, Agent, or Firm* — K&L Gates, LLP; Louis Cullman; Georgia Kefallinos

(57) ABSTRACT

Provided is a unit which is capable of readily grinding and collecting a small amount of a sample which is difficult to be ground. The unit for grinding a sample comprises a club-shaped pestle and a mortar into which the pestle can be inserted, wherein the pestle comprises a roughened taper located at at least one end of its pestle body, wherein the mortar is a tube with an inverted frustoconical bottom, and the surface of the mortar where the taper of the pestle contacts the inverted frustoconical bottom when the pestle is inserted into the mortar is roughened, and wherein the angle of the taper with respect to the longitudinal centerline of the pestle is substantially equal to the angle of the inner wall of the inverted frustoconical bottom with respect to the longitudinal centerline of the mortar. The roughened taper and surface improve grinding efficiency.

6 Claims, 8 Drawing Sheets

(56) References Cited

FOREIGN PATENT DOCUMENTS

| JP | 1-152721 | 10/1989 |
| JP | 2003-220345 | 8/2003 |
| JP | 2005-246155 | 9/2005 |
| JP | 2007-218903 | 8/2007 |

* cited by examiner

UNIT FOR GRINDING SAMPLE, UNIT FOR GRINDING AND COLLECTING SAMPLE, AND PROCESS FOR GRINDING SAME

CROSS-REFERENCE TO RELATED APPLICATION

This application claims the benefit of Japanese Patent Application No. 2011-123592, filed on Jun. 1, 2011, the entire disclosure of which is incorporated by reference herein.

FIELD

The present invention relates to: a unit for grinding a sample such that the unit comprises a club-shaped pestle and a mortar into which the pestle can be inserted; a unit for grinding and collecting a sample such that the unit comprises the unit for collecting a sample and a receptacle for collecting the sample; and to a process for grinding a sample.

BACKGROUND

In an experiment, uniform grinding of a sample of an animal or plant tissue and extraction of the components of the tissue to analyze the components has been widespread. Conventionally, a mortar and a pestle have been used to grind a sample, but the conventional mortars and pestles are not suitable for efficiently handling a very small amount of a sample or various samples because the conventional mortars are large. Units for efficiently grinding a small amount of a sample and various samples include a grinding unit that places a grinder of a particular shape into a vessel and moving the vessel in the figure eight pattern to grind the sample in the vessel (see Patent Literature 1: Japanese Patent No. 3834554). In the unit described in Patent Literature 1, the grinder of a particular shape is placed into the elongated vessel, together with a sample to be ground, and the vessel is moved in the figure eight pattern. As a result, the grinder repeatedly hits the bottom of the vessel while relatively rotating. Thus the vessel and the grinder act as a mortar and a pestle respectively to effectively grind the sample.

There is also a unit for grinding a sample by inserting the sample and a plunger into a tube with a filter at the bottom; rotating the plunger to crush the sample; pressing the plunger; and centrifuging the tube and the plunger to force the sample to pass through the filter to yield the fine particles (see Patent Literature 2: Japanese Patent No. 3853794). According to Patent Literature 2, the grinding process comprises pressing the sample using the plunger and thus can achieve a higher collection of the ground sample and a higher security than the process of only applying centrifugal force to force the sample to pass through the filter to yield the fine particles. And the unit according to Patent Literature 2 can simultaneously grind plural samples and thus can improve operating efficiency.

The unit described in Patent Literature 1, however, is required to move the vessel which contains a sample in the figure eight pattern to grind the sample. Thus it is necessary to prepare a special grinding tool which can provide such movement. This means that conventional tools cannot be used in the unit and that the installation is costly and time consuming. Additionally, the grinder is made of magnetic stainless steel such as SUS430, hard stainless steel such as SUS304, titanium, tungsten, glass, or the like. The grinder is required to be washed and/or the like for next use, which may cause contamination or reduce the maneuverability. Furthermore, because a sample is ground only when the grinder falls onto the vessel under its own weight, some samples are difficult to be sufficiently ground.

On the other hand, the grinding process described in Patent Literature 2 comprises rotating a pressing member which is provided with protrusions extending radially at the bottom thereof to crush a sample between the pressing member and the filter, and then passing the ground sample through the filter by centrifugation. The process is suitable for grinding relatively flexible tissues such as brain and liver tissues. Additionally, the unit is made of plastic and thus is disposable to prevent contamination. A fibrous tissue such as a muscle tissue, however, cannot be sufficiently ground only with the protrusions formed on the bottom of the pressing member as described above. Even when the ground tissue is subsequently centrifuged, such tissue is difficult to be passed through the filter to yield the fine particles, and thus the collection of the tissue may be reduced.

SUMMARY

In view of the foregoing, it is an object of the present invention to provide a unit for grinding a sample and a unit for grinding and collecting a sample which are disposable to prevent contamination and which can efficiently grind a tissue sample which contains many fibers or the like; and a process for grinding a sample using such unit.

The present inventors have closely examined conventional grinding units and have found that even if a grinding unit is made of synthetic resin, roughening of the contact surface between the mortar and the pestle allows a sample to be crushed and ground; that the use of a tube with a bottom surface as the mortar allows the ground sample to be collected at the bottom of the tube; that the use, as the mortar, of a tube with an openable bottom, the opening being provided with a filter, allows the fine particles to be yielded and allows the coarse particles to be left on the filter by centrifuging the ground sample to force the sample to pass through the filter, which means that the fine and the coarse particles can be readily separated; and that placement of the mortar into a receptacle for collecting a sample and centrifugation of the receptacle allow the ground sample to be accumulated at the bottom of the receptacle, which means that the ground sample can also be readily collected. Consequently the inventors have completed this invention.

The present invention provides a unit for grinding a sample, such that the unit comprises a club-shaped pestle and a mortar into which the pestle can be inserted, wherein the pestle comprises a roughened taper located at at least one end of a pestle body; wherein the mortar is a tube with an inverted frustoconical bottom, and the surface of the mortar where the taper of the pestle contacts the inverted frustoconical bottom when the pestle is inserted into the mortar is roughened; and wherein the angle of the taper with respect to the longitudinal centerline of the pestle is substantially equal to the angle of the inner wall of the inverted frustoconical bottom with respect to the longitudinal centerline of the mortar.

The invention also provides the unit for grinding a sample as described above, wherein the taper of the pestle comprises a spiral groove and/or the pestle body comprises a spiral protrusion.

The invention also provides the unit for grinding a sample as described above, wherein the lower end of the inverted frustoconical bottom of the mortar is openable, and the filter is disposed via a fastener in the opening of the openable end.

The invention also provides the unit for grinding a sample as described above, wherein the pestle passes through an antispill feature which has a smaller diameter than the inner diameter of the mortar.

The invention also provides a unit for grinding and collecting a sample, which the unit comprises the unit for grinding a sample as described above and a tubular receptacle for collecting the sample, the receptacle being capable of containing the unit for grinding a sample.

The invention also provides a unit for grinding and collecting a sample as described above, wherein the unit further comprises a feature which prevents rotation of the mortar in the receptacle.

The invention also provides a unit for grinding a sample, which the unit comprises a club-shaped pestle and a mortar into which the pestle can be inserted, wherein the pestle comprises a rubbing region which is a roughened surface located at at least one end of the pestle; wherein the mortar is a tube with a bottom surface; wherein the bottom surface substantially conforms with the rubbing region when the pestle is inserted into the mortar; and wherein the inner wall of the mortar comprises a roughened surface where the rubbing region contacts the inner wall.

The invention also provides a process for grinding a sample using a unit for grinding a sample which the unit comprises a mortar and a pestle, wherein the pestle is a club-shaped pestle with a roughened taper located at at least one end thereof; wherein the mortar is a tube with an inverted frustoconical bottom, the end of the bottom being openable; wherein a filter is disposed via a fastener in the opening of the openable end; wherein the surface where the taper of the pestle contacts the inverted frustoconical bottom when the pestle is inserted into the mortar is roughened; and wherein the process comprises placing a sample and the pestle into the mortar, pressing and rotating the pestle to crush the sample with the roughened surfaces of the pestle and the mortar, and centrifuging the ground sample to force the sample to pass through the filter to more crush the sample and to yield the fine particles.

According to the invention, the grinding unit crushes and grinds a sample with the roughened surfaces of the pestle and the mortar and thus the unit can grind a fibrous tissue. Additionally, when the mortar is a tube with a bottom surface and a filter disposed via a fastener at the bottom, the ground sample is further allowed to pass through the filter to yield the fine particles and to leave the coarse particles on the filter, thereby readily separate the fine particles.

When the unit for grinding and collecting a sample according to the invention comprises an inverted frustoconical bottom, the unit can efficiently grind and collect a small amount of a sample.

Because the unit for grinding a sample according to the invention can be made of synthetic resin, the unit is lighter and more maneuverable than conventional mortars and pestles. Additionally, the unit according to the invention can be manufactured cheaply and thus the unit can be intended to be used only once, thereby efficiently preventing contamination of the sample.

BRIEF DESCRIPTION OF THE DRAWINGS

A more complete understanding of this application can be obtained when the following detailed description is considered in conjunction with the following drawings, in which:

FIG. 2C is a bottom view of the mortar;

FIGS. 7A to 7D illustrate another embodiment of a unit for grinding and collecting a sample according to the invention, in which FIG. 7A is a side view which shows an embodiment of a receptacle for collecting a sample, the receptacle comprising a screw cap, FIG. 7B is a side view which shows an embodiment of inserting a unit for grinding a sample according to the invention into the receptacle for collecting a sample shown in FIG. 7A, FIG. 7C illustrates the state of the unit for grinding and collecting a sample after the insertion, and FIG. 7D further illustrates the state of the unit for grinding and collecting a sample after the screw cap is screwed, with the cross section shown on the left and the side view shown on the right.

DETAILED DESCRIPTION

Figures 1A, 1B, 1C:
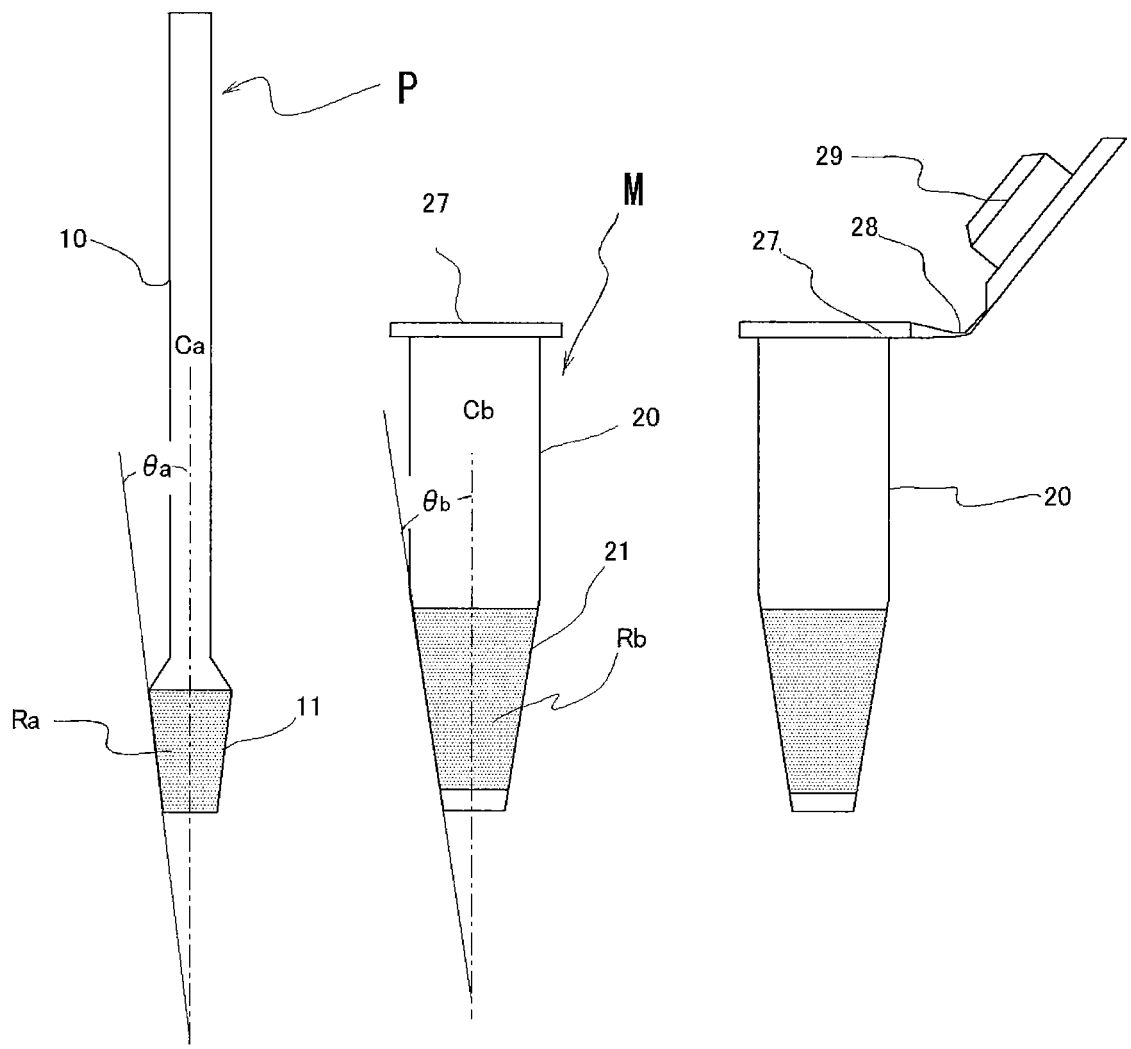
FIGS. 1A to 1C illustrate a unit for grinding a sample according to the invention, which the unit comprises a tubular mortar comprising a mortar body with an inverted frustoconical bottom, and a club-shaped pestle comprising a tapered grinding end.

The first embodiment of the invention is a unit for grinding a sample, which the unit comprises a club-shaped pestle and a mortar into which the pestle can be inserted, wherein the pestle comprises a rubbing region which is a roughened surface located at at least one end of a pestle body; wherein the mortar is a tube with a bottom surface; wherein the bottom surface is substantially conforms with the rubbing region when the pestle is inserted into the mortar; wherein the surface where the rubbing region contacts the inner wall of the mortar when the pestle is inserted into the mortar is roughened. The rubbing region may be in the form of a taper. When the rubbing region is in the form of a taper, preferably the mortar is a tube with an inverted frustoconical bottom, wherein the surface where the taper of the pestle contacts the inverted frustoconical bottom when the pestle is inserted into the mortar is roughened, and wherein the angle of the taper with respect to the longitudinal centerline of the pestle is substantially equal to the angle of the inner wall of the inverted frustoconical bottom with respect to the longitudinal centerline of the mortar. Because of the roughened taper and surface, pressing and rubbing of the rubbing region of the pestle against the roughened surface of the mortar allow a sample in the mortar to be ground. The mortar may also be a tube with an openable end of the inverted frustoconical bottom and a filter disposed via a fastener in the opening of the openable end.

The second embodiment of the invention is a unit for grinding and collecting a sample, which the unit comprises the unit for grinding a sample as described above, the unit comprising an openable end of the inverted frustoconical bottom and a filter disposed via a fastener in the opening of the openable end; and a tubular receptacle for collecting the sample, the receptacle being capable of containing the unit for grinding a sample.

The third embodiment of the invention is a process for grinding a sample using a unit for grinding a sample wherein the unit comprises a mortar and a pestle, wherein the pestle is a club-shaped pestle with a roughened taper located at at least one end of the pestle body; wherein the mortar comprises an inverted frustoconical bottom, an openable end of the inverted frustoconical bottom, and a filter disposed via a fastener in the opening of the openable end; and wherein the surface of the mortar where the taper of the pestle contacts the inverted frustoconical bottom when the pestle is inserted into the mortar is roughened; and wherein the process comprises placing a sample and the pestle into the mortar, pressing and rotating the pestle to crush the sample with the roughened surfaces of the pestle and the mortar, and centrifuging the ground sample to force the sample to pass through the filter to more crush the sample and to yield the fine particles.

Hereinafter, the invention will be described with reference to the drawings.

(1) Unit for Grinding Sample and Unit for Grinding and Collecting Sample (i) Unit for Grinding Sample The unit for grinding a sample according to the invention comprises a club-shaped pestle and a mortar into which the pestle can be inserted.

The pestle is club-shaped and comprises a rubbing region which is a roughened surface located at at least one end of the pestle body. The mortar is a tube with a bottom surface which substantially conforms with the rubbing region when the pestle is inserted into the mortar. And the inner wall of the mortar comprises a roughened surface where the rubbing region contacts the inner wall when the pestle is inserted into the mortar.

For convenience, the invention will be described with reference to a unit for grinding a sample, the unit comprises a pestle with a rubbing region in the form of a taper, unless otherwise specified. FIGS. 1A to 1C show an example of the suitable embodiments of a unit for grinding a sample according to the invention. FIG. 1A is a front view of the pestle (P), and FIG. 1B is a front view of the mortar (M). As shown in FIGS. 1A to 1C, pestle (P) comprises rod-like pestle body (10) with a rubbing region, which is taper (11), located at at least one end thereof. On the other hand, the mortar (M) is a tube which comprises mortar body (20) with an inverted frustoconical bottom. In place of the mortar (B) shown in FIG. 1B, the invention may use a mortar which comprises a top flange (27) connected via a hinge (28) to a lid (29). Such an embodiment is shown in FIG. 1C.

In the invention, the angle of the taper with respect to longitudinal centerline (Ca) of said pestle (P) (Angle θa) is substantially equal to the angle of the inner wall of the inverted frustoconical bottom with respect to longitudinal centerline (Cb) of said mortar (M) (Angle θb). When said pestle (P) is inserted into the mortar (M), the outer surface of said taper (11) of said pestle (P) contacts the inner surface of the mortar (M). Thus rotation of the pestle (P) allows the taper (11) to be rubbed against the mortar (M). In the invention, said taper (11) of the pestle (P) comprises a roughened outer surface (Ra), and the inner wall of the mortar (M) comprises a roughened surface (Rb) where the taper (11) contacts the mortar (M) when the pestle (P) is placed into the mortar (M). Thus when a sample is placed into the mortar (M), and then the pestle (P) is inserted onto the sample and pressed and rotated, the sample can be crushed and ground with the roughened surface (Ra) of the pestle (P) and the roughened surface (Rb) of the mortar (M).

Furthermore, the unit for grinding a sample according to the invention comprises an inverted frustoconical bottom of the mortar (M), the bottom corresponding to the taper of said rubbing region, and thus the unit can readily collect even a small amount of a sample from the bottom. To collect the ground sample, the mortar (M) with the pestle (P) inserted may be centrifuged together with the ground sample to allow the sample to be accumulated at the bottom of mortar (M), and then the accumulated sample may be collected. Because the ground sample is accumulated at the bottom by centrifugal force, almost all of the sample can be collected.

Figures 2A, 2B, 2C:
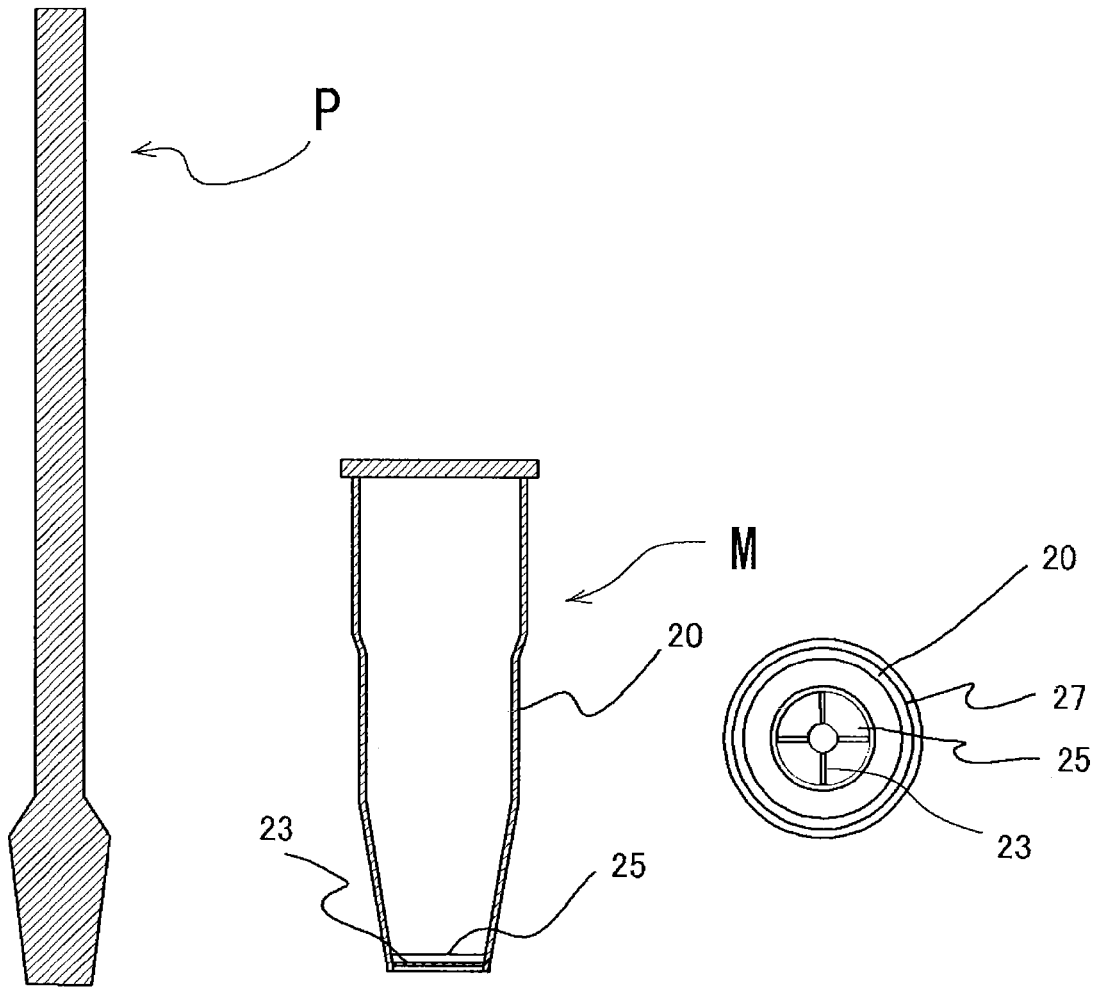
FIGS. 2A to 2C illustrate a unit for grinding a sample according to the invention, which the unit comprises a mortar comprising an inverted frustoconical bottom with an openable end, a fastener disposed in the opening of the bottom, and a filter fixed via the fastener; and a club-shaped pestle comprising a tapered grinding end.

As shown in the cross sectional view of FIG. 2B and the bottom view of FIG. 2C, the mortar (M) used in the unit for grinding a sample according to the invention may comprise an openable end of the inverted frustoconical bottom, the opening comprising fastener (23) via which filter (25) is fixed. In such case, the sample placed into the mortar (M) can be ground by pressing and rotating pestle (P) in the same way of FIGS. 1A to 1C. Although the ground sample on filter (25) may be collected using a sterile spoon or the like, the mortar (M) with pestle (P) contained may be placed into a test tube or the like and then be centrifuged to force the sample to pass through filter (25) to yield the fine particles. Because the coarse particles are left on filter (25), the process described above allows the fine particles to be readily separated from the coarse particles. Furthermore, because the fine particles pass through filter (25) and accumulate at the bottom of the test tube or the like, the process described above allows the ground particles to be readily collected. Additionally, if filter (25) is fixed to the inverted frustoconical bottom of the mortar (M), the degree of crush can be adjusted by appropriately selecting the pore diameter of filter (25). FIG. 2A is a longitudinal sectional view of pestle (P), and FIG. 2B is a longitudinal sectional view of the mortar (M).

(ii) Unit for Grinding and Collecting Sample

Figures 3A, 3B, 3C:
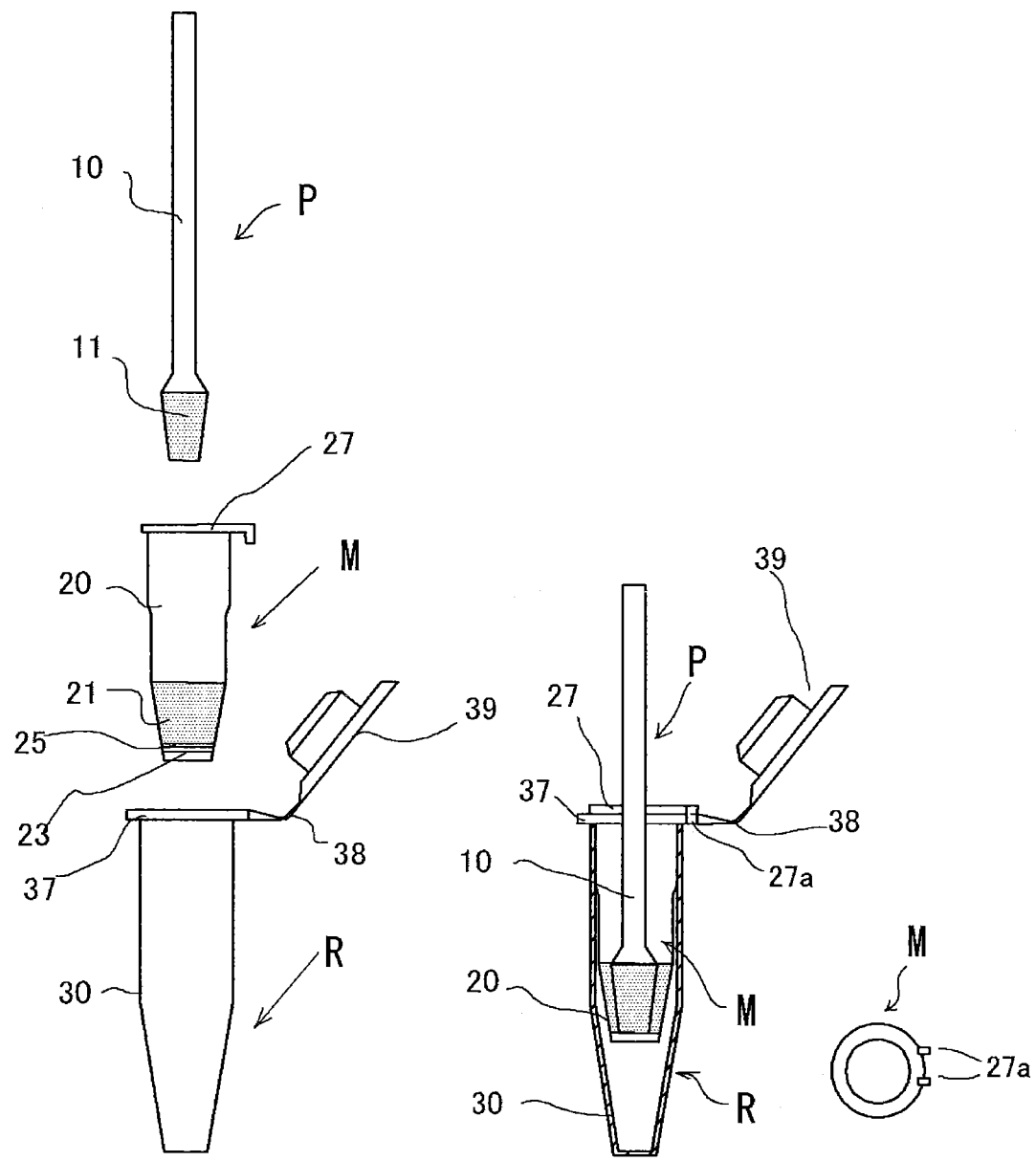
FIGS. 3A to 3C illustrate a unit for grinding and collecting a sample according to the invention, which the unit comprises in combination a unit for grinding a sample, the unit comprising the mortar and the pestle as shown in FIGS. 2A to 2C, and a tubular receptacle for collecting the sample.

As shown in FIG. 3A, the pestle (P) and mortar (M) which comprises a filter (25) disposed via a fastener (23) at the bottom can be combined with a tubular receptacle (R) for collecting a sample to provide the unit for grinding and collecting a sample as shown in FIG. 3B. FIG. 3B is a cross sectional view of the unit for grinding and collecting a sample, with a receptacle (R) containing the mortar (M) with the filter (25) fixed via the fastener (23) at the bottom of the mortar (M) and with pestle (A) contained in the mortar (M). Because a filter through which a sample can be passed is disposed at the bottom of the mortar (M), the sample can be transferred from the mortar to the receptacle (R) for collecting the sample by centrifugal force. If the pestle (P) is pressed and rotated to crush and grind the sample, the ground sample may be collected from the top surface of the filter (25) of the mortar (M). But if after grinding, the mortar (M) is placed into the receptacle (R) and then centrifuged, the sample can be accumulated at the bottom of the receptacle (R). Because this embodiment uses the dedicated receptacle (R) for collecting a sample, the mortar (M) can be placed into the receptacle (R) before grinding a sample with pestle (P). Then, after grinding, the unit for collecting and grinding a sample is centrifuged to force the sample to pass through the filter to more crush the sample and to yield the fine particles.

Although the tools for the unit for grinding a sample and the unit for collecting and grinding a sample according to the invention can have any size, the mortar (M), for example, has preferably a volume of 0.1-100 ml, more preferably a volume of 0.5-80 ml, and still more preferably a volume of 1-50 ml. The diameter, length, and the like can be optionally selected within the range described above. The invention allows a small amount of a sample to be efficiently ground and allows the ground sample to be readily collected.

The samples that can be ground using the unit for grinding a sample or the unit for grinding and collecting a sample according to the invention can include relatively flexible tissues such as brain and liver tissues; animal tissues including muscle fibers; leafs, stems, roots, and seeds of a plant; insects; fishes; seashells; bacteria; yeasts; and the like.

(2) Pestle

Pestle (P) used for the invention is club-shaped and comprises a grinding end, which is the rubbing region, and a holding end.

The pestle can made of synthetic resin including polyolefin resin such as polyethylene, polypropylene and polystyrene; polyester such as polyethylene terephthalate; polyacetal; polyethylene fluoride; and polycarbonate. A cylindrical grinding aid can be made of synthetic resin including silicone resin; polyolefin resin such as polyethylene, polypropylene and polystyrene; polyester resin such as polyethylene terephthalate; polyethylene fluoride resin; and polycarbonate resin.

Although a mortar and pestle which comprise a roughened surface have been conventionally used to grind a sample, they have been heavy and expensive. And there have been no mortar and pestle made of synthetic resin. In the invention, it is found that use of the pestle (P) and the mortar (M) which are made of synthetic resin and which comprise a roughened surface (R) allows a fibrous tissue such as a muscle tissue to be ground.

Conventional pestles for grinding a sample comprise a generally sphere shaped end and such pestles are pressed and rubbed to crush and grind a sample. And such pestles are moved in a circle around the sphere shaped end and thus the pestles are suitable for grinding a large amount of a sample. When the conventional pestles are used to grind a small amount of a sample, however, the ground particles spread over the large surface of the sphere shaped end, and thus the particles are difficult to be collected. On the other hand, when the pestle (P) used for the invention comprises a rubbing region which is a tapered grinding end, rotation of the pestle (P) around the longitudinal central axis allows the sample to be readily ground.

The angle of the taper with respect to the longitudinal centerline of the pestle (P) (angle θa) is preferably 5-85°, more preferably 5-60°, and still more preferably 5-30°. Particularly, the taper angle (θa) is preferably equal to or smaller than the angle of the inner wall of the inverted frustoconical bottom of the mortar (M) (angle θb) as described above. When the angle θa is smaller than the angle θb, the angle θa differs from the angle θb by preferably 0-20°, more preferably 0-5°, and still more preferably 1-3°. If the difference exceeds 20°, the contact area between the pestle and the inner wall of the mortar is reduced and thus the grinding effect when the pestle is rotated may be reduced. On the other hand, when the angle θa is larger than the angle θb, the pestle cannot be inserted into the inverted frustoconical bottom of the mortar, and thus it may be difficult to sufficiently grind a sample.

According to the invention, the taper of the synthetic resin pestle as described above is roughened. As measured as a maximum height (Rz) in accordance with JIS B 0601 (2001), the taper has a degree of roughness of 1-300 μm, preferably 5-200 μm, more preferably 10-100 μm. The maximum height (Rz) of the taper may be the same as or different from that of the mortar. Such roughening can be achieved by plasma processing, general dimpling such as etching and sandblasting, or texturing.

In addition to the taper (11) of the grinding end of the inverted frustoconical bottom, a region above the inverted frustoconical end and taper (11) may be roughened. Because a sample is ground by pressing and rotating the pestle (P), roughening of the inverted frustoconical end can further improve the grinding efficiency.

According to the invention, the taper (11) of pestle (P) grinds a sample in cooperation with the roughened inner wall of the mortar (M). The size of the taper (11) can be appropriately selected depending on the size of the mortar (M).

Figures 4A, 4B, 4C:
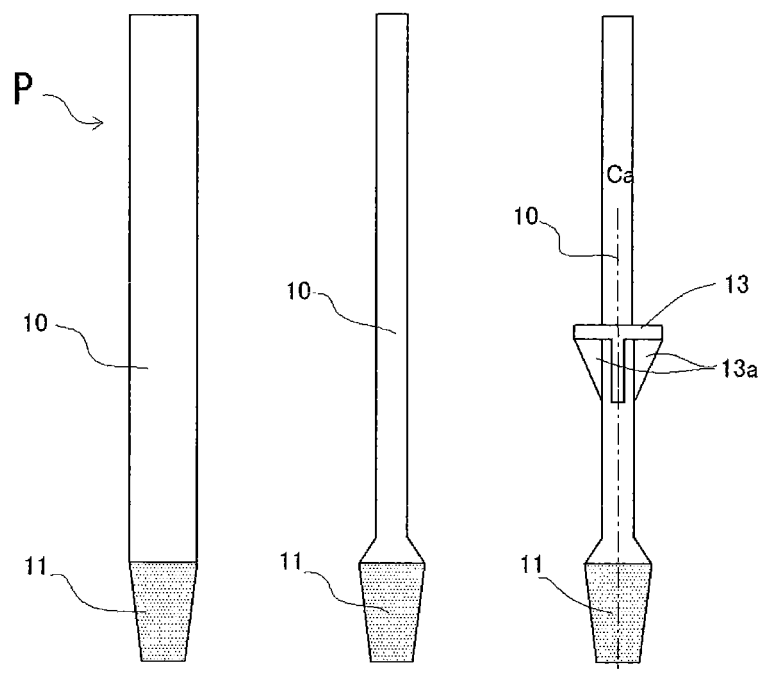
FIGS. 4A to 4C illustrate another embodiment of the pestle of a unit for grinding a sample according to the invention.

As shown in FIG. 4A, the pestle (P) used for the invention may comprise the taper (11) at the grinding end, the taper becoming narrower toward the end of the pestle. As shown in FIG. 4B, the pestle may comprise a thin pestle body (10) which becomes wider near the grinding end and taper (11) connected to the wider portion of the pestle body (10). As shown in FIG. 4C, the pestle (P) may pass through antispill feature (13) which has a smaller diameter than the inner diameter of the mortar (M) and which is concentric with centerline (Ca) of the pestle (P). Additionally, said antispill feature (13) may be fixed to the pestle body (10) with plural supporters (13a). If the pestle comprises such antispill feature (13), the sample can be efficiently prevented from spilling out during grinding. Especially when a pathogenic sample is ground, prevention of the spill of the sample can assure the safety of the operator and can avoid contamination of the surrounding atmosphere. Said antispill feature (13) has preferably a size such that antispill feature (13) can be contained inside the mortar (M) when pestle (P) is inserted into the mortar (M). The inner wall of the mortar (M) and the periphery of antispill feature (13) allow the pestle (P) which is inserted into the mortar (M) to be held approximately centered.

Figures 5A, 5B, 5C, 5D, 5E:
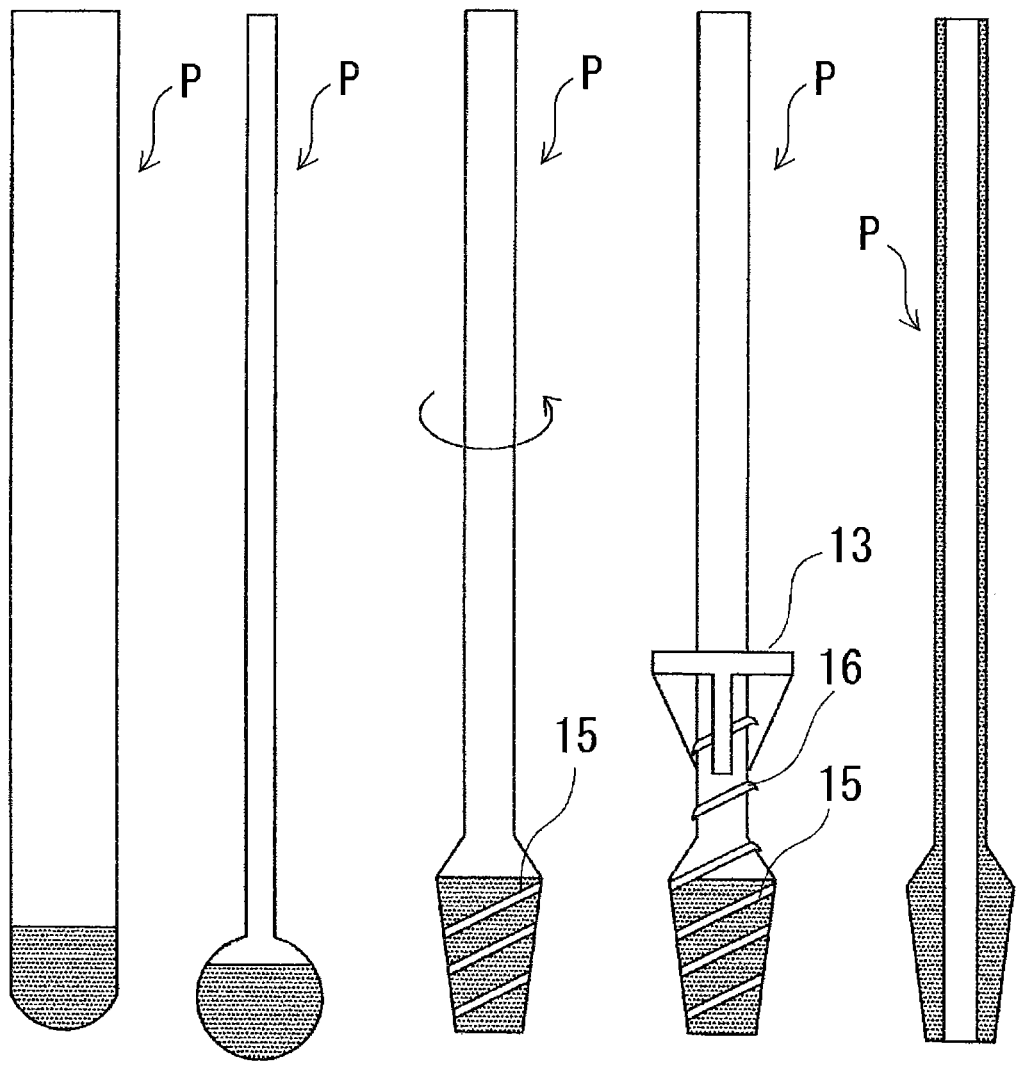
FIGS. 5A to 5E illustrate another embodiment of the pestle used in the invention.

As described above, the pestle is club shaped and may be in any form as long as the pestle comprises a rubbing region which is a roughened surface located at at least one end of the pestle body. For example, the pestle may comprise a circular end as shown in FIG. 5A or a spherical end which has a larger diameter than that of the pestle body as shown in FIG. 5B. In the figures, the roughened surface is shaded in a dotted pattern. The pestle (P) used in the invention may also comprise spiral groove (15) on the surface of said rubbing region. As shown in FIG. 5C, when spiral groove (15) rotates from the bottom left to the top right of the taper, rotation of the pestle (P) in the direction of the arrow shown in FIG. 5C forces the sample toward the narrower end of the taper and thus forces the sample to be moved toward the bottom of the mortar (M), thereby efficiently grind the sample. In place of or in addition to said spiral groove (15), the pestle body (10) may comprise spiral protrusion (16). FIG. 5D shows an embodiment of the pestle (P) which comprises an antispill feature (13), a spiral groove (15) in the taper, and a spiral protrusion (16) extending from above the taper to the lower end of the antispill feature (13). The spiral protrusion (16) may also be inclined toward the narrower end of the taper such that the rotation of the pestle (P) forces the sample toward the narrower end of the taper.

The pestle (P) is not limited to the cylindrical pestle shown in FIG. 2A, and may comprise a cavity as shown in FIG. 5E.

Figure 6A:
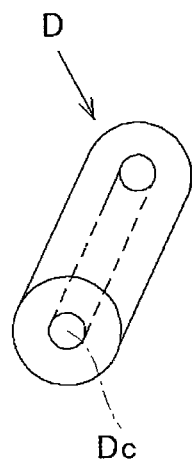
FIGS. 6A and 6B illustrate a grinding aid which can aid in rotating a pestle used in the invention.
Figure 6B:
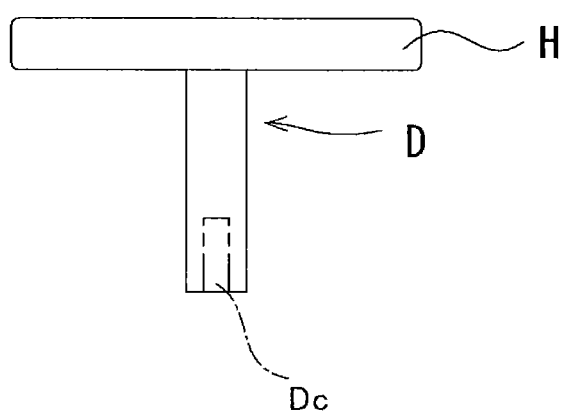

The holding end of the pestle (P) may comprise knurls which are arranged circumferentially in a geodesic pattern or may be in the form of a polygonal column, such that the users can readily rotate the pestle (P). The holding end may be provided with a separate grinding aid which aids in rotating the pestle (P). Such a grinding aid can include, for example, a hollow and thick cylindrical aid (D) as shown in FIG. 6A. If the pestle body (10) is passed through the cavity (Dc) of cylindrical aid (D) and said cylindrical aid (D) is held when a sample is ground, the pestle can be easily held and rotated, thereby facilitating grinding of a large amount of a sample. Such cylindrical grinding aid can be made of synthetic resin including silicone resin; polyolefin resin such as polyethylene, polypropylene and polystyrene resin; polystyrene resin; polyester resin such as polyethylene terephthalate; polyethylene fluoride resin; and polycarbonate resin. And as shown in FIG. 6B, the grinding aid may comprise a cylinder (D) and a gripper (H) perpendicular to the cylinder (D). Additionally, the grinding aid may be an electric device for rotating the pestle or the like.

(3) Mortar

Mortar (M) used in the invention is a tube with a bottom surface, wherein the bottom surface substantially conforms with said rubbing region when said pestle is inserted into the mortar, and wherein the inner wall of the mortar comprises a roughened surface where said rubbing region contacts the inner wall. When pestle (P) comprises a taper, the mortar comprises a tubular mortar body (20) with an inverted frustoconical bottom and roughened surface (Rb) where taper (11) of said pestle (P) contacts the inverted frustoconical bottom when said pestle (P) is inserted into mortar (M).

(i) Material and Surface Treatment

Mortar (M) can be made of synthetic resin including polyolefin resin such as polyethylene and polypropylene; polyacetal; polystyrene; polyester such as polyethylene terephthalate; polyethylene fluoride; and polycarbonate. The material may be the same as or different from that of pestle (P). It has been found that roughened surface (R) of synthetic resin mortar (M) allows a fibrous tissue such as a muscle tissue to be ground.

Said mortar body (20) comprises an inverted frustoconical bottom when pestle (P) comprises a tapered rubbing region. When pestle (P) is inserted into mortar (M), tapered end (11) of pestle (P) reaches the inverted frustoconical bottom of mortar body (20), where the sample contained in mortar (M) is ground. To achieve efficient grinding, the angle of the inner wall of the inverted frustoconical bottom with respect to longitudinal centerline (Cb) of mortar (M) (angle θb) is preferably 5-85°, more preferably 5-60°, and still more preferably 5-30°. In grinding with a conventional mortar and a conventional pestle, the rough surface of the pestle is rubbed against the bottom of the mortar. Thus conventional mortars have generally a substantially sphere-shaped bottom. In contrast, an object of the unit for grinding a sample according to the invention is to efficiently grind a small amount of a sample, and thus such unit can efficiently grind a sample by rotating its pestle around the longitudinal centerline thereof. Thus the mortar is provided with an inverted frustoconical bottom and angle θb is set to 5-85°. If the angle were less than 5°, it would be difficult to provide a capacious mortar and to grind a large amount of a sample. If the angle were more than 85°, it might be difficult to grind a sample by pressing and rotating pestle (P).

The invention is characterized in that the inner wall of the inverted frustoconical bottom is roughened. As measured as a maximum height (Rz) in accordance with JIS B 0601 (2001), the inner wall has preferably a degree of roughness of 1-300 μm, more preferably 5-200 μm, and still more preferably 10-100 μm. If the roughness were less than 1 μm, it would be less easy to crush a sample. If the roughness were more than 300 μm, the sample might be undesirably contaminated with abraded protrusions during grinding. Roughening can be achieved by plasma processing, general dimpling such as etching and sandblasting, or texturing.

The inner wall of mortar (M) is roughened in order to crush and grind a sample by rubbing pestle (P) against the inner wall of mortar (M). Thus roughened surface (Rb) of the inner wall of mortar (M) at least extends across the rubbed region where pestle (P) contacts the wall during grinding. As used herein, the term "rubbed region" refers to the region where the outer surface of the rubbing region of pestle (P) contacts mortar (M) when pestle (P) is inserted into mortar (M) and then pestle (P) is pressed or rotated to grind a sample. For example, when the rubbing region is a taper, the roughened surface is not limited to the region where taper (11) of pestle (P) contacts mortar (M) when pestle (P) is inserted into mortar (M). Also, the roughened surface may have a smaller area than that of the rubbed region against which pestle (P) rubs, and may be limited to only a portion of the rubbed region, as long as a sample can be sufficiently ground. Because a roughened surface causes reduction in visibility of the sample in the mortar, a smaller roughened surface allows the grinding state to be readily checked.

The bottom of mortar (M) substantially conforms with the rubbing region of pestle (P) when pestle (P) is inserted into mortar (M). When pestle (P) comprises a circular or spherical end as shown in FIG. 5A or 5B respectively, mortar (M) also comprises a circular bottom. In such embodiment, the rubbed region also refers to a region where the outer surface of the rubbing region of pestle (P) contacts mortar (B) when pestle (P) is inserted into mortar (M) and pestle (P) is pressed or rotated to grind a sample. And such region is roughened.

As shown in FIGS. 1B and 1C, mortar (M) used in the invention may comprise a closed bottom (such mortar is hereinafter also referred to as "closed bottom mortar (M1)"). As shown in FIG. 2B, mortar (M) may comprise an openable inverted frustoconical bottom, fastener (23), and filter (25) disposed via fastener (23) (such mortar is also referred to as "filtered bottom mortar (M2)").

(ii) Filter

Filter (25) has an outer diameter slightly larger than the inner diameter of filtered bottom mortar (M2), and is mounted on fastener (23) on the inner periphery of mortar (M2). Filter (25) is a 1-3 mm thick hard filter made of polypropylene or glass which is provided with pores with a diameter of the cross section perpendicular to the axis of 1-300 μm. The degree of grinding or crushing can be adjusted by appropriately selecting the pore size. According to the grinding or crushing purpose, plural filters with different pore sizes may be laminated. Filter (25) may be a commercially available filter. For example, a polypropylene filter from Porex, Germany, a glass filter from Sibata Scientifict Technology Ltd., and the like may be used.

(iii) Other Structures

The grinding process may vary depending on whether filter (25) is disposed at the bottom of mortar (M). Thus the other structures of closed bottom mortar (M1) without a filter as illustrated in FIG. 1B and of filtered bottom mortar (M2) with a filter as illustrated in FIG. 2B will be separately described.

When a sample and then pestle (P) is placed into closed bottom mortar (M1) to grind the sample, the ground sample is accumulated at the bottom of mortar (M1). After pestle (P) is removed from mortar (M1), mortar (M1) can be used as a sample storage container. For example, as shown in FIG. 1C, lid (29) is preferably connected via hinge (28) to top flange (27) of mortar (M1). This allows the moisture contained in the ground sample to be prevented from evaporating and allows prevention of contamination. Mortar (M1) may further comprise a memory to identify the content.

On the other hand, filtered bottom mortar (M2) is characterized by comprising an openable inverted frustoconical bottom which is provided with fastener (23). The bottom view of FIG. 2C shows an embodiment which comprises a cross shaped fastener (23) at the bottom of filtered bottom mortar (M2). But fastener (23) may have any shape, as long as the fastener can fix filter (25). For example, fastener (23) may be in the form of a network or may form a dotted pattern in the opening, as long as the inverted frustoconical bottom is openable and filter (25) can be fixed. Furthermore, fastener (23) may be integrated with or separate from mortar body (20), as long as fastener (23) can fix filter (25).

Before grinding a sample, mortar (M2) used in the invention can be placed into receptacle (R) for collecting the sample. In order to facilitate positioning mortar (M2) in receptacle (R), fixing mortar (M2) to receptacle (R), and removing mortar (M2) from receptacle (R) after use, flange (27) is preferably integrated with the top end of mortar (M2). The bottom of flange (27) can be fastened to flange (37) of receptacle (R) when a sample is ground. This allows mortar (M2) to be readily removed from receptacle (R) after grinding a sample.

Figures 7A, 7B, 7C, 7D:
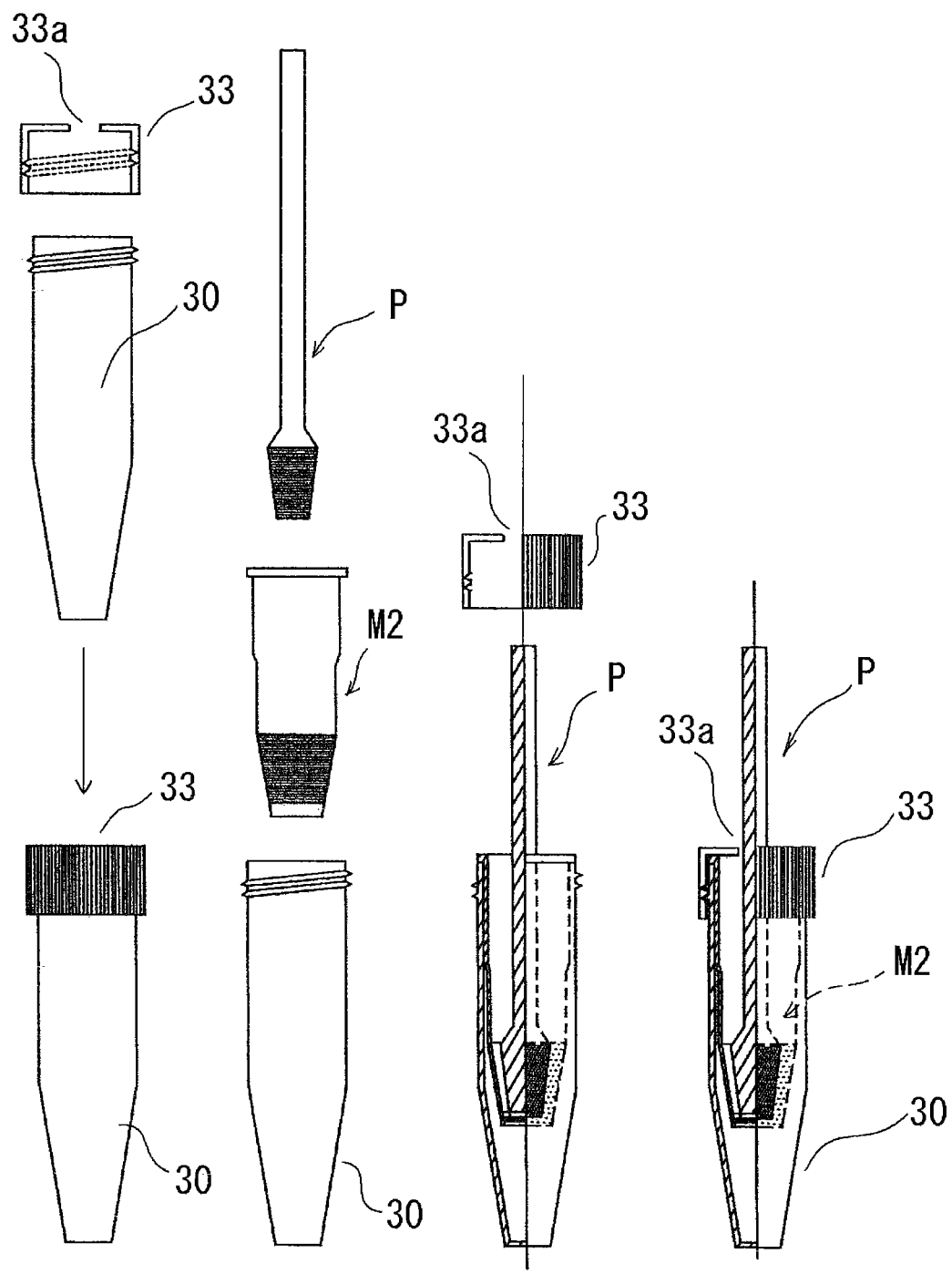

The unit for collecting and grinding a sample according to the invention preferably comprises a feature for preventing rotation of mortar (M2) in said receptacle for collecting a sample. For example, when receptacle (R) comprises lid (39) connected via hinge (38) to flange (37) as shown in FIG. 3A, mortar (M2) can comprise, as the antirotation feature, nail like fasteners (27a) which can engage hinge (38). FIG. 3C shows a pair of nail like fasteners (27a) on the periphery of flange (27), the fasteners being spaced at a certain distance and extending toward the lower end. Nail like fasteners (27a) can be connected to the both ends of hinge (38) of receptacle (R) to position and fix mortar (M2) in receptacle (R), thereby preventing rotation of mortar (M2) in receptacle (R) during grinding and thus achieving stable grinding operation. Such antirotation feature can be appropriately selected depending on receptacle (R). For example, when receptacle (R) is screwed receptacle (30) with screwed lid (33) as shown in FIG. 7A, provision of hole (33a) on the center of screw lid (33) for passing pestle (P) through allows mortar (M2) to be prevented from rotating. Mortar (M2) which contains a sample and pestle (P) are placed into screwed receptacle (30) as shown in FIG. 7B, and pestle (P) is passed through hole (33a) of screwed lid (33) from the upper end of pestle (A) as shown in FIG. 7C. Then screwed lid (33) is screwed onto screwed receptacle (30) as shown in FIG. 7D. When screwed lid (33) is screwed, mortar (M2) is pressed onto the upper end of screwed receptacle (30), thereby preventing rotation of mortar (M2).

Figures 8A, 8B, 8C:
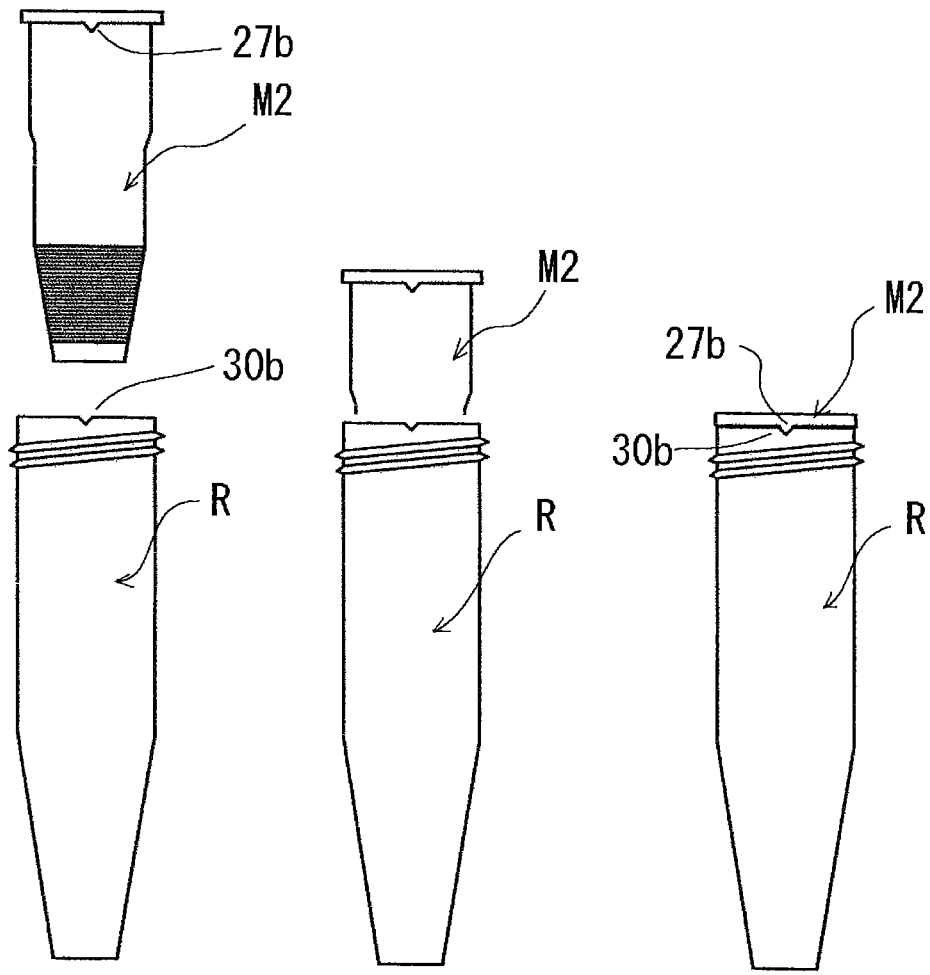
FIGS. 8A to 8C illustrate combination of a receptacle for collecting a sample and a unit for grinding a sample according to the invention, which constitute a unit for grinding and collecting a sample according to the invention.

Furthermore, as shown in FIG. 8A, screwed receptacle (30) may comprise wedged groove (30b) at the top end thereof and mortar (M2) may comprise wedged protrusion (27b) on the lower end of flange (27) which the protrusion can engage said wedged groove (30b). When mortar (M2) is inserted into screwed receptacle (30) as shown in FIG. 8B, wedged groove (30b) engages protrusion (27b) as shown in FIG. 8C, which allows mortar (M2) to be further sufficiently prevented from rotating. The protrusion and the groove may be rectangular or circular in place of wedge, as long as they can prevent rotation of mortar (M2) in screwed receptacle (30). And the number of the protrusion and the groove is not limited to one, and thus plural protrusions and grooves may be provided.

The antirotation feature is also not limited to those as described above. For example, a spiral similar to that formed on said lid may be integrally formed on the periphery of top flange (27) of mortar (M2). And such spiral can be used as the antirotation feature by screwing said lid in the similar manner to said tube.

(4) Receptacle for Collecting Sample

The unit for collecting and grinding a sample comprises tubular receptacle (R) for collecting a sample, which the receptacle is capable of containing said unit for grinding a sample. Combination of said unit for grinding a sample and receptacle (R) allows the ground sample to be directly collected in receptacle (R), and thus allows the ground sample to be readily and safely ground and collected.

Receptacle (R) may be any tube, as long as it can contain the unit for grinding a sample, which the unit comprises said pestle (P) and said mortar (M). Receptacle (R) preferably comprises a lid in order to prevent leaking of the contents, although the lid is not essential. receptacle (R) preferably comprises a bottom with a recess in the center thereof, such as an inverted frustoconical or a hemispherical bottom. Thus the ground sample can be accumulated in the center of the bottom. When receptacle (R) comprises an inverted frustoconical bottom, the angle of the inner wall of the inverted frustum is selected such that receptacle (R) can contain the unit for grinding a sample.

The capacity of receptacle (R) can be appropriately selected depending on the capacity of said mortar (M). Receptacle (R) may have marks on tube (30) to indicate the content. As shown in FIG. 3A, lid (39) is preferably connected via hinge (38) to the top end of tube (30) such that receptacle (R) can be used as a sample storage container after grinding a sample. In place of the lid shown in FIGS. 3A and 3B, a screwed lid may be used. Receptacle (R) may be a commercially available microtube, a test tube onto which a screwed lid is screwed, or a screwed receptacle.

(5) Process for Grinding Sample

The unit for grinding a sample according to the invention can be used to efficiently grind even a small amount of a sample comprising tissues such as muscle tissues. As described above, a process for collecting a sample also varies depending on whether the mortar comprises filter (25) or not. So the process using a closed bottom mortar (M1) and the process using a filtered bottom mortar (M2) will be described separately.

(i) Grinding Process Using a Closed Bottom Mortar (M1)

When a closet bottom mortar (M1) is used as a mortar (M), a sample is placed in from the end of the mortar (M1) with a flange (27), and then a pestle (P) is placed into the mortar (M1). Next, the pestle (P) is pressed and rotated to grind the sample. A buffer or physiologic saline may be added to the sample for grinding. Because the ground sample adheres to the inner wall of the mortar (M1) and the taper (11) of the pestle (P), the ground sample can be collected by scratching the sample with pestle (P). A buffer may also be added to the sample to collect the sample as a suspension. Additionally, after grinding, the mortar (M1) with pestle (P) inserted may be centrifuged on a centrifuge or the like to accumulate the ground sample at the bottom of the closed bottom mortar (M1). Then pestle (P) can be removed from the mortar (B1) to directly collect the sample in the mortar (M1). If a lid (29) is connected to the top end of the mortar (M1), the lid can seal the opening of the mortar (M1) to prevent contamination or drying of the contents.

(ii) Grinding Process Using a Filtered Bottom Mortar (M2)

When a filtered bottom mortar (M2) is used as the mortar (M), first, the mortar (M2) with filter (25) fixed via fastener (23) can be placed into receptacle (R) and then a sample and pestle (P) can be placed into the mortar (M2) to grind the sample. When the mortar (M2) comprises a flange (27) on its top end, the lower surface of said flange (27) can be connected to the top of the flange (37) of the receptacle (R) to dispose the filtered bottom mortar (M2) in receptacle (R) without closely contacting the bottom of mortar (M2) with the bottom of receptacle (R). When a pair of nail like fasteners (27a) is disposed on flange (27) of mortar (M2), the pair of nail like fasteners (27a) can be connected to the both ends of hinge (38) of receptacle (R) to position and fix mortar (M2) in receptacle (R). Such positioning and fixing prevent rotation of mortar (M2) in receptacle (R), thereby allowing efficient grinding.

The process for grinding using mortar (M2) is the same as the process using mortar (M1). A buffer or physiologic saline may be added to the sample. Because the ground sample adheres to the inner wall of mortar (M2) and taper (11) of pestle (P), the ground sample can be collected by scratching the ground sample with pestle (P). A buffer may also be added to the ground sample to collect the sample as a suspension. Additionally, after grinding, mortar (M2) with pestle (P) inserted may be centrifuged on a centrifuge or the like to force the ground sample to pass through filter (25) and then to be accumulated at the bottom of receptacle (R). Then pestle (P), together with mortar (M2), can be removed from receptacle (R) to directly collect the sample in receptacle (R). If lid (39) is connected to the top of receptacle (R), the lid can seal the opening of receptacle (R) to prevent contamination or drying of the contents. Because the ground sample passes through filter (25), the fine particles can be yielded and at the same time, the fine particles can be readily separated from the coarse particles.

When mortar (M2) is used, pestle (P) may be pressed and rotated to grind a sample and then the ground sample is scratched with pestle (P) or another tool to collect the sample without using receptacle (R), as in the process using the mortar (M1). But if mortar (M2) is not centrifuged, it is not expected that the fine and the coarse particles can be separated, and the sample are more crushed and finer particles can be yielded by passing the sample through filter (25).

According to the invention, centrifugation of the ground sample allows the sample to be more crushed and finer particles to be yielded, and thus the invention can simplify a process for grinding a sample, compared to a process in which all of the grinding steps are manually carried out. Because plural receptacles (R) can be placed on a centrifuge, plural samples can be simultaneously centrifuged to collect the ground samples, thereby improving operation efficiency.

Preferably a sample is ground and centrifuged in a cooling atmosphere. This allows prevention of thermal modification of the sample due to frictional heat or the like generated during grinding, prevention of degradation by endogenous enzyme or the like, and extraction of a substance of interest from a "homogenized" sample without breakage.

EXAMPLES

The invention will be specifically described with reference to the examples, although the invention is not limited to the examples.

Example 1

A protein was extracted from the liver of a mouse by using a unit for grinding a sample as shown in FIGS. 1A and 1B, the unit comprising a polyacetal club-shaped pestle with a length of 68 mm, a taper angle (θa) of 9°, and a roughened surface with a maximum height (Rz) of 68-73 μm in accordance with JIS B 0601 (2001), and a polypropylene mortar with a full length with the lid of 40 mm, an inverted frustoconical bottom, a taper angle (θb) of 10°, and a roughened surface with a maximum height (Rz) of 68-73 μm in accordance with JIS B 0601 (2001).

The liver of a mouse was cut into about 80 mg and placed into the mortar. Then 1 ml of Trizol reagent (from Life Technologies) was added. The pestle was inserted into the mortar and then pressed and rotated to crush and grind the liver tissue.

The ground particles were separated by centrifugation with the pestle inserted into the mortar, and then the pestle was removed from the mortar. After removing the coarse particles and the lipid from the centrifuged particles, the mass of the protein was determined to be 21.27 mg by the Bradford assay.

Comparative Example 1

The same unit was used as in example 1, except that the unit had no roughened surface. And the mass of the protein was determined to be 17.28 mg as measured in the same manner as example 1.

Example 2

About 50 mg each of the liver and the kidney of a mouse was ground using the same unit with roughened surfaces as that used in example 1. And RNA was extracted from the ground samples.

The 50 mg each of the liver and the kidney of a mouse was placed into the mortar and then 1 ml of Trizol reagent (from Life Technologies) was added to the sample. Then the pestle was inserted into the mortar and pressed and rotated to crush and grind the sample.

Then the ground particles were separated by centrifugation, and the coarse particles were removed. Next, RNA was extracted from the particles, and the concentration of the extracted RNA was determined with a spectrophotometer. The results are shown in Table 1.

Example 3

RNA was extracted from the liver and the kidney of a mouse using a unit for grinding and collecting a sample, the unit comprising a polypropylene receptacle for collecting a sample as shown in FIG. 3A with a full length with the lid of 40 mm, a polypropylene mortar as shown in FIGS. 2A to 2C with a length of 30 mm, an inverted frustoconical bottom with a polypropylene filter having a diameter of 3 mm, a thickness of 1.5 mm, and a pore diameter of the cross section perpendicular to the axis of 70-130 μm, a taper angle (θb) of 12°, and a roughened surface with a maximum height (Rz) of 68-73 μm in accordance with JIS B 0601 (2001), and a polyacetal club-shaped pestle with a length of 65 mm, a taper angle (θa) of 11°, and a roughened surface with a maximum height (Rz) of 68-73 μm in accordance with JIS B 0601 (2001).

The mortar is placed into the receptacle. Each of the liver and the kidney of a mouse was cut into about 50 mg and inserted into the mortar. Next, 200 μl of Trizol reagent (from Life Technologies) was added. Then the pestle was inserted into the mortar and pressed and rotated to crush and grind the sample.

The unit with the pestle inserted into the mortar was centrifuged. Then the mortar and the pestle were removed. 800 μl of Trizol reagent was added and the ground particles were collected from the bottom of the receptacle. Then RNA was extracted from the collected particles. The concentration of the extracted RNA was determined with a spectrophotometer. The results are shown in Table 1.

Comparative Example 2

Liver and kidney tissue were ground using BioMasher I from Nippi Co., Ltd. as a unit for grinding a sample of FIG. 4 in Patent Literature 2. The filter used in the unit was made of polypropylene and had a diameter of 6 mm, a thickness of 1 mm, and a pore diameter of the cross section perpendicular to the axis of 70-130 µm.

The filter was disposed in grinding tube 11 before grinding, and the tissue and 200 µl of Trizol reagent were added onto said filter 12. Then grinding pestle 20 was slidably placed into the tube from the opening to seal the opening. Grinding tube 11, together with grinding pestle 20, was inserted into tube 40 for collecting a sample and then centrifuged. After centrifugation, the grinding tube and grinding pestle 20 were removed and 800 µl of Trizol reagent was added. The ground particles were collected from the bottom of tube 40, and RNA was extracted from the collected particles. The concentration of the extracted RNA was determined with a spectrophotometer. The results are shown in Table 1.

Example 4

RNA was extracted and the concentration of the extracted RNA was determined in the same manner as example 3, except that 50 mg of a heart tissue was used as a sample. The results are shown in Table 2.

Comparative Example 3

RNA was extracted and the concentration of the extracted RNA was determined in the same manner as comparative example 2, except that 50 mg of a heart tissue was used as a sample. The results are shown in Table 2.

TABLE 1

| | Amount of Extracted RNA (µg) | | |
|---|---|---|---|
| | Example 2 | Example 3 | Comparative Example 2 |
| Liver | 100.2 | 183.5 | 97.2 |
| Kidney | 93.6 | 95.8 | 85.5 |

TABLE 2

| | Amount of Extracted RNA (µg) | |
|---|---|---|
| | Example 4 | Comparative Example 3 |
| Heart tissue | 13.4 | 2.21 |

(Results)

(1) The results of example 1 and comparative example 1 show that even when a soft tissue such as a liver tissue was used, the mass of the protein extracted using a pestle and a mortar with a roughened surface in example 1 was 1.2 times greater than the mass of the protein extracted using the tools without a roughened surface in comparative example 1. Thus it has been found that a roughened surface can improve grinding efficiency.

(2) The results of examples 2 and 3 and comparative example 2 show that the unit for grinding a sample according to the invention, the unit comprising a filter, a pestle with a roughened surface, and a mortar with a roughened surface can efficiently extract RNA from a soft tissue such as a liver tissue. Specifically, it is presumed that because the ground sample was passed through the filter to yield the fine particles, the amount of the extracted RNA increased compared to the data on the unit for grinding a sample in example 2, the unit comprising a pestle with a roughened surface, and a mortar with a roughened surface without a filter. The amount of the extracted RNA in example 2 was similar to that in comparative example 2. This shows that a pestle with a roughened surface and a mortar with a roughened surface can grind a sample at the same level as the case in which the ground sample is passed through a filter.

(3) The results of example 4 and comparative example 3 show that when a fibrous tissue such as a heart tissue was ground in example 4 using the unit for grinding a sample according to the invention, the unit comprising a pestle with a roughened surface and a mortar with a roughened surface, the unit could extract RNA 6 times more than comparative example 3 in which the sample was only passed through a filter.

Having described and illustrated the principles of this application by reference to preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. A unit for grinding a sample comprising:
    a club-shaped pestle including a roughened surface on at least one end of the pestle; and
    a mortar comprising an inverted frustoconical bottom including a lower end that is openable comprising a filter which is fixed to the mortar by a fastener;
    wherein the sample is derived from at least one of an animal tissue or a plant tissue;
    wherein the pestle is configured to be inserted into the mortar and wherein the roughened surface contacts the inverted frustoconical bottom;
    wherein the angle of the roughened surface with respect to the longitudinal centerline of the pestle is equal to the angle of the inner wall of the inverted frustoconical bottom with respect to the longitudinal centerline of the mortar;
    wherein the pestle is configured to force the sample through the filter to yield fine particles when centrifuged together with the sample; and
    wherein the unit for grinding the sample further comprises a tubular receptacle for collecting the sample, the receptacle being capable of containing the mortar.

2. The unit for grinding a sample according to claim 1, wherein the roughened surface comprises at least one of a spiral groove or a spiral protrusion.

3. The unit for grinding a sample according to any one of the preceding claims, wherein the pestle passes through an antispill feature which has a smaller diameter than the inner diameter of the mortar.

4. A unit for grinding a sample according to claim 1, further comprising a feature which prevents rotation of the mortar in the receptacle.

5. The unit for grinding the sample according to claim 1, wherein the degree of roughness of the roughened surface of the club-shaped pestle is 1-300 μm.

6. The unit for grinding the sample according to claim 1, wherein the sample includes muscle fibers.

\* \* \* \* \*